United States Patent
Kousalik et al.

(10) Patent No.: US 10,197,548 B2
(45) Date of Patent: Feb. 5, 2019

(54) METHOD OF ADJUSTMENT OF A WORKSTATION AND A YARN CLEARER (YARN QUALITY SENSOR) ON A YARN MANUFACTURING TEXTILE MACHINE

(71) Applicant: Rieter CZ s.r.o., Usti nad Orlici (CZ)

(72) Inventors: Pavel Kousalik, Usti nad Orlici (CZ); Petr Haska, Usti nad Orlici (CZ); Zdenek Beran, Lanskroun (CZ)

(73) Assignee: Rieter CZ s.r.o., Usti nad Orlici (CZ)

( * ) Notice: Subject to any disclaimer, the term of this patent is extended or adjusted under 35 U.S.C. 154(b) by 208 days.

(21) Appl. No.: 15/342,640

(22) Filed: Nov. 3, 2016

(65) Prior Publication Data
US 2017/0122926 A1 May 4, 2017

(30) Foreign Application Priority Data

Nov. 3, 2015 (CZ) .................................. 2015-773

(51) Int. Cl.
| | |
|---|---|
| *G01N 33/36* | (2006.01) |
| *B65H 63/06* | (2006.01) |
| *D01H 13/22* | (2006.01) |
| *D01H 13/26* | (2006.01) |

(52) U.S. Cl.
CPC ........... *G01N 33/365* (2013.01); *B65H 63/06* (2013.01); *D01H 13/22* (2013.01); *D01H 13/26* (2013.01); *B65H 2701/31* (2013.01)

(58) Field of Classification Search
CPC .. G01N 33/365; B65H 63/06; B65H 2701/31; D01H 13/22; D01H 13/26
See application file for complete search history.

(56) References Cited

U.S. PATENT DOCUMENTS

| | | | | |
|---|---|---|---|---|
| 3,438,188 | A | * | 4/1969 | Boggs ................ B65H 63/028 57/81 |
| 3,673,591 | A | | 6/1972 | Peyer |
| 4,056,926 | A | | 11/1977 | Stüber |
| 4,817,425 | A | | 4/1989 | Ueda et al. |
| 5,537,811 | A | * | 7/1996 | Pidoux ................ B65H 63/062 28/226 |
| 5,799,476 | A | | 9/1998 | Bahlmann |

(Continued)

FOREIGN PATENT DOCUMENTS

| | | |
|---|---|---|
| CZ | 288653 B6 | 11/1995 |
| EP | 2 690 047 B1 | 1/2014 |
| WO | WO 2005/047155 A1 | 11/1995 |

OTHER PUBLICATIONS

Czech Republic Search Report, dated Jun. 29, 2016.

*Primary Examiner* — Lisa Caputo
*Assistant Examiner* — Irving A Campbell
(74) *Attorney, Agent, or Firm* — Dority & Manning, P.A.

(57) ABSTRACT

A method is provided for adjustment of a textile machine workstation based on yarn parameters measured by an associated yarn quality sensor at the work station. The method generates a first reference value of a selected yarn parameter by measurement of the yarn parameter or by calculation, wherein the first reference value is generated from the yarn parameter for a deliberately defective yarn intentionally produced at the workstation. The method then compares a current value or second reference value of the yarn parameter for yarn produced at the workstation of production quality or higher-than-production quality to the first reference value.

8 Claims, 2 Drawing Sheets

(56) References Cited

U.S. PATENT DOCUMENTS

| | | | | |
|---|---|---|---|---|
| 5,832,709 A | * | 11/1998 | Lassmann | B65H 69/00 57/263 |
| 6,244,030 B1 | * | 6/2001 | Arb | B65H 63/065 57/264 |
| 6,374,152 B1 | * | 4/2002 | Wepfer | B65H 63/062 700/130 |
| 6,798,506 B2 | * | 9/2004 | Furter | G01N 21/8915 356/238.2 |
| 7,424,800 B2 | | 9/2008 | Biermann et al. | |

* cited by examiner

METHOD OF ADJUSTMENT OF A WORKSTATION AND A YARN CLEARER (YARN QUALITY SENSOR) ON A YARN MANUFACTURING TEXTILE MACHINE

TECHNICAL FIELD

The invention relates to a method of adjustment of a workstation and a yarn clearer (a yarn quality sensor) at a workstation of a textile machine, in which measurement and/or calculation creates a reference value of a particular yarn parameter, to which the current value of the particular parameter measured during continuous yarn production is compared.

BACKGROUND

The basic function of a yarn clearer (yarn quality sensor) on a yarn making textile machine is detecting yarn defects during yarn production. Nowadays, the evaluation of whether a yarn parameter which is detected in real-time during yarn production by the clearer (yarn quality sensor) is to be considered a defect is basically carried out by three different methods.

The first method is the so-called absolute method, in which a current yarn parameter, such as thickness, unevenness, is determined, e.g. by measurement or calculation, and this parameter is compared in an absolute manner to a set defect level. If the determined parameter or absolute deflection of the determined parameter, i.e. the absolute value of the difference between the measured and desired (set) parameter, exceeds the set limit (set fault level), this is assessed as a yarn defect and, if appropriate, subsequent measures are taken to remove the defect.

The disadvantage of the absolute method is the fact that it cannot be used for those defects for which the correct or desired absolute value of the parameter is not known, for which a relative change in the parameter is evaluated, or this value is dependent on the particular workstation at which yarn is produced. Typically, such defects include long defects of yarn (sliver defects, defects related to the yarn count or more).

The second method is the so-called relative group method, in which the yarn parameter measured or calculated is compared to the mean value of the same yarn parameter measured by a group of clearers (yarn quality sensors) or it is compared to the parameter calculated for a group of clearers (yarn quality sensors). The group of clearers (yarn quality sensors) is on the same machine and the workstations which produce the same yarn. If the difference or relative deflection between the measured or calculated parameter of the clearer (yarn quality sensor) being evaluated and the mean value of the same parameter calculated from the data of the above-mentioned group of clearers (yarn quality sensors) exceeds the set limit, this state is assessed as a yarn defect and, if appropriate, subsequent measures are taken to remove the defect.

The drawback of using the relative group method is the fact that this evaluation is not appropriate for defects for which even on yarn without defects too broad a range of the values of the particular parameter is recorded at the individual workstations. In extreme cases, using the relative group method leads to the difference between the correct and defective value of the yarn parameter at one workstation is smaller than the variation range (maximum-minimum) of this parameter for a group of workstations. Such typical defects are yarn unevenness and hairiness.

The third method is the so-called relative individual method, in which the measured or calculated parameter of each clearer (yarn quality sensor) in real-time is compared to the "correct", i.e. reference value of the parameter of the particular workstation. If the difference between the measured and the individual reference value of the particular workstation, or a relative deflection of the determined parameter from the individual reference value of the particular workstation exceeds the set limit, this state is assessed as a yarn defect and, if appropriate, subsequent measures are taken to remove the defect. The above-mentioned "correct", i.e. reference value is obtained either by calculation or by measuring the correct, i.e. reference yarn at the particular workstation, at which yarn is produced and which applies this "correct", i.e. reference value for cleaning production yarn or for monitoring the quality of production yarn. At present, in most cases this type of individual reference parameter is determined when first starting the workstation with new operating values (yarn count, twist, etc.) at which the parameter is evaluated, or the reference parameter is determined each time the workstation is started, after the first spinning-in operation on an empty tube and, in case of need, corrections are made to the reference parameter even during the ongoing production of yarn.

The disadvantage of the relative individual method consists in determining the reference value of the parameter, to which the measured or calculated parameter is to be compared. It is the determination of the reference value of the parameter that is a critical moment. The main reason is that there is a considerable risk that during the determination of the reference value, i.e. during measurement of the parameter for the determination of the reference value, defective yarn is produced, which, however, cannot be classified as defective, since the system of the clearer (yarn quality sensor) actually "does not know" that it is measuring defective yarn, since it does not have the reference value (which is being determined during this measurement process), against which it makes a decision as to whether the yarn being produced is faultless or defective. Such typical defects include, for example, defects caused by a failure of the moistening system of yarn during yarn production on an air-jet spinning machine, when a lack of water manifests itself in increased yarn hairiness, which has no effect on the yarn clearer or the sensor of yarn quality and therefore such a defect cannot be automatically detected. A similar situation may occur when the pressure drops in the spinning nozzle during the production of yarn on an air-jet spinning machine.

SUMMARY OF THE INVENTION

The aim of the invention is therefore to eliminate or at least minimize the disadvantages of the background art, especially to allow detecting defects that are not detectable by the existing systems. Additional objects and advantages of the invention will be set forth in part in the following description, or may be obvious from the description, or may be learned through practice of the invention.

The aim of the invention is achieved by a method of adjustment of a yarn clearer (sensor of yarn quality) on a yarn manufacturing textile machine, whose principle consists in that a reference value of a particular yarn parameter is determined as the reference value of the particular yarn parameter from a defective yarn deliberately produced at the particular workstation. This value is subsequently compared to the current or reference value of the particular parameter of yarn produced at the particular workstation, having production quality or higher than production quality.

By means of the values of the particular parameter obtained during simulated (intentional) occurrence of a defect and during the production of faultless yarn it is possible to adjust better the clearer (yarn quality sensor) for measuring the particular parameter for the phase of normal production of yarn at the particular workstation. Also, it is possible to test the correct function of the sensor and the workstation. Moreover, it is even possible to adapt the centrally set parameters of cleaning yarn to the individual work station.

DESCRIPTION OF DRAWINGS

The invention is schematically represented in the drawing, where.

DETAILED DESCRIPTION

Figure 1:
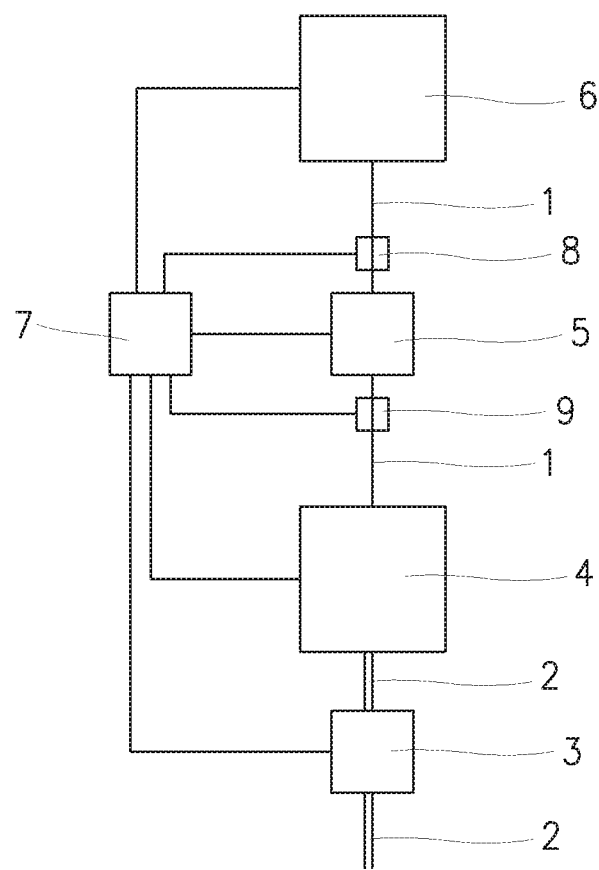
FIG. 1 shows an arrangement of a workstation.

Reference will now be made to embodiments of the invention, one or more examples of which are shown in the drawings. Each embodiment is provided by way of explanation of the invention, and not as a limitation of the invention. For example features illustrated or described as part of one embodiment can be combined with another embodiment to yield still another embodiment. It is intended that the present invention include these and other modifications and variations to the embodiments described herein.

The invention will be described on an exemplary embodiment on a textile machine comprising a row of workstations, arranged next to each other, for the production of yarn 1 and winding yarn 1 on a bobbin.

First of all, each workstation comprises in the direction of the movement of fibers 2 in the process of yarn formation means 3 for feeding fibers 2 to a unit 4 for yarn 1 formation.

Fibers 2 are fed to the production process of yarn 1 in a suitable form, e.g. in the form of a roving or sliver, etc.

The means 3 for feeding fibers 2 to the unit 4 for yarn 1 formation are either independent and are arranged before the unit 4 for yarn 1 formation, e.g., a drafting device of an air-jet spinning machine, or they are part of the unit 4 for yarn 1 formation, e.g., a feeding device of a spinning unit of an open-end spinning machine, etc.

The unit 4 for yarn 1 formation for instance comprises an unillustrated spinning rotor or a spinning nozzle, in which yarn 1 is formed from the fibers being fed.

Behind the unit 4 for yarn 1 formation are arranged means 5 for drawing off yarn 1, e.g. known unillustrated drawing-off rollers. Behind the means 5 for drawing off yarn 1 are arranged means 6 for winding yarn 1 on an unillustrated bobbin, including unillustrated means for transversing yarn across the width of the bobbin when winding yarn on the bobbin.

The individual units 4, means 3, 5, 6 and other nodes of the workstation, or the individual or at least some of their working elements are connected to a control system, namely either to a control system of the respective unit and/or workstation and/or machine section and/or to the control system of the entire machine—generally speaking, they are connected to the control system 7. The specific arrangement and hierarchy of the individual parts of the control system 7 is highly variable and as such it is not the subject of this solution.

At least one sensor 9 of yarn 1 quality is arranged between the unit 4 for yarn 1 formation and the means 6 for winding yarn 1 on the bobbin. The sensor 9 of yarn 1 quality is part of the system for monitoring the quality of the produced yarn 1, which measures the characteristics and evaluates the yarn quality and after revealing a defect in the yarn 1 makes a decision about removing the defect and, if necessary, ensures that the defect is removed. In the illustrated embodiment, a yarn 1 quality sensor 9 is arranged between the unit 4 for yarn 1 formation and the means 5 for drawing off yarn 1. Also, in the illustrated embodiment between the means 5 for drawing off yarn 1 and the means 6 for winding yarn 1 on the bobbin is arranged a yarn presence sensor 8. In an illustrated embodiment, the yarn 1 quality sensor 9 is arranged between the means 5 for drawing off yarn 1 and the means 6 for winding yarn 1. In another unillustrated embodiment, only one yarn 1 sensor is arranged at the workstation, namely the yarn 1 quality sensor 9. In another unillustrated embodiment at least a pair of yarn 1 quality sensors 9 is arranged at the workstation. Both the yarn 1 quality sensor 9 and the yarn 1 presence sensor 8 are connected to the control system 7.

The invention is based on a special modification of an individual method of evaluation and its application for such defects in the yarn 1, which can be artificially generated (simulated) at the workstation. The yarn 1 quality sensor 9 monitors the produced yarn 1, measures or calculates the current value of a selected parameter P of the produced yarn 1 and from the measured values, the reference (e.g. mean) values of the selected parameter $P_R$ are determined. Moreover, the selected parameter P of the produced yarn 1 is monitored in different operating modes F, I, M of the particular workstation and by means of absolute and/or relative comparison of parameters P, $P_R$ it is possible to achieve a more accurate evaluation of the quality of the produced yarn 1, the evaluation being adaptable to each workstation.

The first operating mode is a defect mode F, in which the current value $P_f$ of the particular yarn parameter of a deliberately defective yarn 1 intentionally produced at the particular workstation is monitored and the reference (e.g. mean) value of the particular parameter $P_{fR}$ of the deliberately defective yarn 1 intentionally produced at the particular workstation is determined (e.g. by calculation). The values of the particular parameter $P_f$ and $P_{fR}$ of the deliberately defective yarn 1 are measured by the yarn 1 quality sensor 9 at the particular workstation and calculated after the means of the workstation, or at least one of them, are intentionally set in such a manner that the workstation deliberately produces defective yarn 1, i.e. a defect in the yarn 1 is simulated. It is therefore a method based on creating a defect in the yarn 1 artificially (deliberately) by the setting of at least one working means, node, part, etc., of the particular workstation and on detecting the influence of this artificially induced defect in the yarn 1 on the current value $P_f$ of the particular yarn parameter of the deliberately defective yarn 1, which is performed by the yarn 1 quality sensor 9. A typical example of intentionally induced production of defective yarn 1 at the workstation is deliberately lowered operating pressure in the spinning nozzle, purposely turned off, or limited supply of the moistening liquid for moistening the yarn 1 during its production, intentionally reduced rotation speed of the spinning rotor, intentionally reduced speed of the drawing-off mechanism of yarn, intentionally reduced or increased supply of fibers to the unit 4 for yarn 1 formation, etc. Sometimes it is favorable to divide this defect mode F of the operation of the particular workstation into several parts, during which artificial (simulated) defects of different sizes and/or of different types, etc., are generated and evaluated. This can be achieved, e.g., by a successive change in the setting of at least one working means (e.g. by setting in steps) or also by successive different setting of different working means.

The second mode is an initialization mode I, in which the yarn 1 quality sensor 9 at the particular workstation monitors the current value $P_O$ of the particular parameter of the faultless (good) yarn 1 produced at the particular workstation and the initial reference (e.g. mean) value $P_{OR}$ of the particular parameter is calculated. The faultless (good) yarn 1 is such yarn 1 that meets the quality requirements for commercially produced (production) yarn 1 or it has a higher quality than required from commercially produced yarn 1. Sometimes it is advantageous to divide the initialization mode I into two parts, wherein in one part yarn 1 of a higher quality than required from commercially produced yarn 1 (from the viewpoint of the particular parameter P) is produced, and by comparing the obtained values $P_O$, $P_{OR}$ to the values $P_f$, $P_{fR}$ of deliberately defective yarn 1 the correct function of the workstation is tested (meanwhile test of the correct function of the workstation), whereupon in the second part of the initialization mode I, the faultless yarn 1 starts to be produced in a quality which is comparable to or the same as the quality of commercially produced yarn 1 and only then the obtained values $P_O$ and $P_{OR}$ of the particular parameter of yarn 1 are used for the adjustment of the yarn 1 clearer (yarn 1 quality sensor 9).

The third mode is a production mode M, in which commercial yarns 1, i.e. yarns 1 of commercial quality are produced and in which the yarn 1 quality sensor 9 monitors the current value $P_P$ of the particular parameter of actually produced (production, commercial) yarn 1, i.e. during ongoing (continuous) production of yarn 1 and the reference value $P_{PR}$ of the parameter of yarn 1 of commercial quality is determined. If in the initialization phase the value I $P_O$ and $P_{OR}$ the particular parameter of yarn 1 is detected on the faultless yarn 1 of a commercial quality, the value $P_P$ of the parameter of actually produced commercial yarn 1 in a certain manner ranges around the reference value of the particular parameter $P_{OR}$ of the fault-free yarn 1, and so the process of adjustment is performed on the basis of these values. According to another preferred embodiment, during evaluation in this mode, the reference value $P_{OR}$ is not used, but during ongoing commercial production of yarn 1 this reference value is modified, or corrected, e.g. by calculating a moving average for eliminating the consequences of a prolonged increase in the value of the measured parameter P as a result the gradual clogging of the system by supplying a moistening liquid, which gradually increases the value of the measured parameter $P_p$ even during normal spinning without occurrence of defects, etc.

For the evaluation of the particular parameter P it is not important whether at the particular workstation it is the value of the particular parameter $P_f$ of deliberately defective yarn 1 intentionally produced at the particular workstation that is first determined or whether it is the value of the particular parameter $P_O$ of fault-free yarn 1 produced at the particular workstation that is first determined.

By means of absolute and/or relative comparison of the values of the particular parameter P of yarn 1 detected in different modes F, I, M and in different phases of yarn 1 production, it is possible to achieve a substantially more accurate assessment of the quality of the produced yarn 1 for the workstation. In addition, it is possible in this manner to test the correct function of the yarn 1 quality sensor 9 and of the workstation or adapt the centrally set parameters of cleaning yarn 1 to the particular workstation.

From the comparison of the values of parameters $P_f$ and $P_O$ it is possible to determine, for example, the correct function of the respective means of the workstation. If the difference between the values $P_f$ and $P_O$ is not sufficiently great, it can be, e.g., assumed that the particular means of the workstation does not work properly. If, for example, in the defect mode F of intentional defect generation the supply of the moistening liquid of yarn 1 is turned off or restricted, while in the initialization mode I the supply of the moistening liquid is turned on, but it does not produce a sufficient difference between the measured values $P_f$ and $P_O$, it may infer that a defect of the supply of the moistening liquid to the workstation. Moreover, from these parameters ($P_f$ and $P_O$), it is possible to determine (or estimate) the size of any changes in the current values of the particular parameter $P_P$ of the actually produced (commercial) yarn 1 in the event of yarn defect P caused by changing the properties of a working means of the workstation. In this manner, it is possible to determine for each particular workstation an individual range of current values of the particular parameter $P_P$ of actually produced (commercial) yarn 1 at the particular workstation, by which means it is possible to determine the limits of the current values of the particular parameter $P_P$, whereby when reaching or exceeding these limits the produced yarn 1 is already considered defective.

In terms of the operation of the workstation, it is apparent that it is possible to perform the above-described method of adjustment of the yarn clearer 1 (yarn 1 quality sensor) at any time during the work cycle of each workstation. However, it is necessary to separate the deliberately produced defective yarn 1 or, on the contrary, the yarn 1 of intentionally better quality from the commercial yarn 1 and withdraw this deliberately defective yarn or the yarn 1 of intentionally better quality to waste. For this reason, the most suitable phase of the operation of the workstation for performing the above-mentioned method of adjustment of the workstation and the yarn clearer 1 (yarn 1 quality sensor 9) by means of determining the values of the particular parameter $P_f$, $P_O$ and $P_P$ is the phase of the workstation operation known as spinning-in yarn 1 during change from a full bobbin to an empty tube, in other words, a phase in which the wound full bobbin is doffed off the winding means 6, a new empty tube is placed in its place, and the workstation produces yarn 1, which is first withdrawn to a waste and only after that it is passed on to the means 6 for winding yarn 1 on the bobbin. More specifically, the most suitable period for performing the method according to the invention is during the above-mentioned production of yarn 1 withdrawn to waste before being passed on to the means 6 for winding yarn 1 on the bobbin, when during this time period a defect in the yarn 1 is deliberately induced at the particular workstation, i.e. a defect is simulated at the particular workstation in order to determine the values of the particular parameter $P_f$ of the deliberately defective yarn 1 intentionally produced at the particular workstation. Also, "measurement" of the yarn 1 with non-present defect, i.e. the determination of the values of the particular parameter $P_O$ of the fault-free yarn 1, produced at a particular workstation, is carried out and the values obtained are introduced to the control system 7. The control system 7, on their basis, assesses the produced yarn 1 after putting the workstation into fully productive mode (parameter $P_P$), i.e. the mode of continuous production of yarn 1, and so it is possible to reveal even the occurrence of yarn defects which have been simulated and which could not be revealed without prior simulation.

Figure 2:
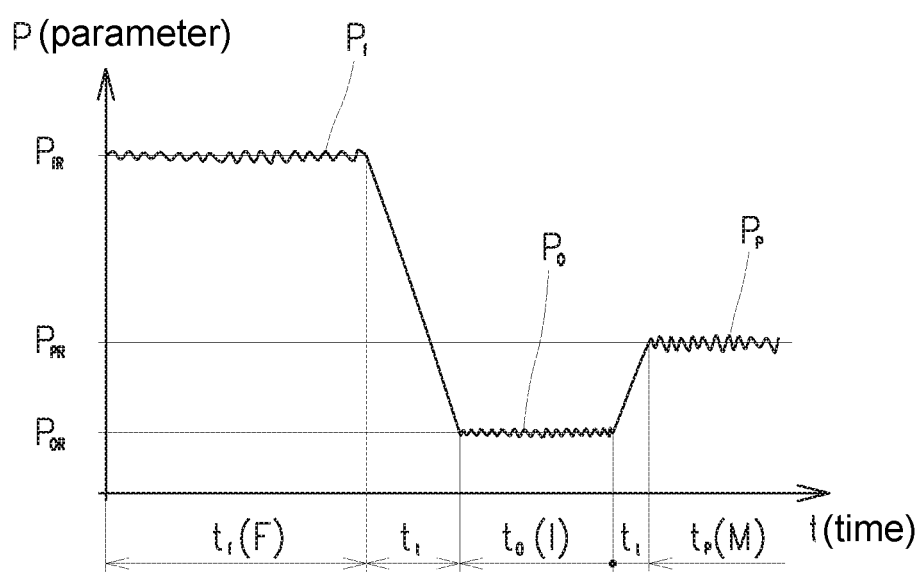
FIG. 2 shows an example of time profile of measured or calculated yarn parameters.

FIG. 2 shows an embodiment, wherein at the particular workstation by means of changing the setting of at least one working means, node, element, a yarn 1 defect is simulated upon the action of the control system 7, during the period $t_f$ (the defect mode F). The yarn 1 defect manifests itself in the current value of the particular parameter $P_f$ of deliberately defective yarn 1 monitored by the yarn 1 quality sensor 9. After recording the current value of parameter $P_f$ and calculating the reference value $P_{fR}$ of the deliberately defective yarn 1 the production status of the fault-free yarn 1 is set by the control device 7 for the working means, nodes, elements, to the status of production of surely fault-free yarn 1 (initialization mode I), a whereby, according to the illustrated embodiment, transition from the status of deliberate production of defective yarn 1, i.e. from the defect mode F, to the status of production of faultless yarn 1, i.e. to the initialization mode I, lasts for a period $t_t$ of transition (transformation). After the transition period $t_t$, faultless yarn 1 is produced at this particular workstation, whereby during the time period $t_0$ the faultless yarn 1 is monitored by the sensor 9 of yarn quality 1, the current values of the particular parameter $P_0$ are recorded and the reference value $P_{0R}$ is calculated (the initialization mode I). In the illustrated embodiment, in the initialization mode I yarn of better quality (better with respect to the parameter P being monitored) is produced than the commercially produced yarn 1 in the subsequent production mode M. After the completion of the initialization phase I, i.e. after the time period $t_0$, the testing of the yarn 1 is terminated and after the time period of the transformation $t_t$ or the time period necessary for the re-adjustment of the means of the workstation for the production of commercial yarn 1 normal (commercial) production of yarn 1 indicated by the time interval $t_p$, is started, (production mode M). If the method according to the present invention is carried out during the process of spinning-in on auxiliary yarn, then the transition of the time interval $t_0$ and the time interval $t_p$ is the time point of passing the newly produced yarn 1 to the means 6 for winding yarn 1 at the particular workstation, and therefore it is also the time point of the termination of the withdrawal of the testing yarn 1 to the waste.

According to the illustrated embodiment, during the adjustment at the particular workstation, one yarn defect 1 is simulated, e.g., only a defect resulting from the defect of feeding the supply of the moistening liquid during yarn production or a defect caused by the pressure drop of the working medium in a spinning nozzle of a spinning machine, and the like. According to an unillustrated embodiment, during adjustment at the particular workstation at least two yarn 1 defects are simulated, e.g., a defect due to the defect of the supply of the moistening liquid during yarn production and a defect caused by the pressure drop of the working medium in the spinning nozzle of the spinning machine, or even more yarn 1 defects caused by an event at the workstation are simulated. The simulation of more yarn 1 defects is either successive, i.e. one defect is simulated after another, or simultaneous, i.e. simultaneously at least two yarn 1 defects are simulated. During a successive simulation of individual defects in the yarn 1 at the particular workstation, sequences are preferably inserted between the individual simulations, during which faultless yarn is produced. During a simultaneous simulation of at least two yarn defects at the particular workstation, e.g. the simultaneous simulation of yarn 1 faults due to the defect in the supply of the moistening liquid during yarn production and, at the same time, due to the pressure drop of the working medium in the spinning nozzle of the spinning machine, etc., is performed.

According to another unillustrated embodiment, during the adjustment at the particular workstation one defect or more types of defect is/are simulated, whereby the size of the simulated defect changes, e.g. the feed of moistening liquid of yarn successively (in several stages) or continuously decreases or the yarn 1 thickness gradually changes by the means 3 for feeding fibers 2 to the unit 4 for yarn 1 formation, etc. This process enables to make the adjustment of the yarn 1 quality sensor 9 more accurate, especially with respect to the detection of small yarn 1 defects and, what is more, it also allows a more accurate adaptation of the centrally set parameters of cleaning yarn 1 to the concrete workstation than during the simulation of a defect of one size.

Modifications and variations can be made to the embodiments illustrated or described herein without departing from the scope and spirit of the invention as set forth in the appended claims.

The invention claimed is:

1. A method for adjustment of a textile machine workstation based on yarn parameters measured by an associated yarn quality sensor at the workstation, comprising:
    generating a first reference value of a selected yarn parameter by measurement of the selected yarn parameter or by calculation, wherein the first reference value is generated from the selected yarn parameter for a deliberately defective yarn intentionally produced at the workstation; and
    comparing a current value or second reference value of the selected yarn parameter for yarn produced at the workstation of production quality or higher-than-production quality to the first reference value.

2. The method according to claim 1, wherein the first reference value is determined from measurement of the yarn by the associated yarn quality sensor at the workstation after intentionally setting at least one device at the workstation to produce the deliberately defective yarn.

3. The method according to claim 1, wherein the first reference value is compared to the second reference value generated from yarn produced at the workstation during fault-free yarn production.

4. The method according to claim 1, wherein the deliberately defective yarn is produced and withdrawn from the workstation without being wound on a bobbin at the workstation.

5. The method according to claim 4, wherein the deliberately defective yarn is produced during changing of a full bobbin with an empty tube at the workstation.

6. The method according to claim 4, wherein the second reference value is determined for the yarn produced at the workstation of production quality or higher-than-production quality before the yarn is passed to a winding device that winds the yarn onto a new bobbin.

7. The method according to claim 4, wherein the deliberately defective yarn is produced during spinning-in of yarn on an auxiliary yarn at the workstation by generating a particular yarn defect, the yarn parameter used to generate the first reference value reflecting the particular yarn defect.

8. The method according to claim 4, wherein the deliberately defective yarn is produced during spinning-in of yarn on an auxiliary yarn at the workstation by generating a particular yarn defect at different levels, or by generating two different yarn defects, the yarn parameter used to generate the first reference value reflecting the particular yarn defects, and the first reference value being generated for the particular yarn defect at each different level, or for each of the different yarn defects.

* * * * *